United States Patent
Takato (10) Patent No.: US 7,978,423 B2
(45) Date of Patent: Jul. 12, 2011

(54) OBJECTIVE OPTICAL SYSTEM FOR ENDOSCOPES

(75) Inventor: Hideyasu Takato, Tokyo (JP)

(73) Assignee: Olympus Medical Systems Corp., Tokyo (JP)

(*) Notice: Subject to any disclaimer, the term of this patent is extended or adjusted under 35 U.S.C. 154(b) by 35 days.

(21) Appl. No.: 12/527,931

(22) PCT Filed: Feb. 26, 2008

(86) PCT No.: PCT/JP2008/053239
§ 371 (c)(1),
(2), (4) Date: Aug. 20, 2009

(87) PCT Pub. No.: WO2008/111386
PCT Pub. Date: Sep. 18, 2008

(65) Prior Publication Data
US 2010/0046093 A1    Feb. 25, 2010

(30) Foreign Application Priority Data
Mar. 9, 2007    (JP) ................ 2007-060145

(51) Int. Cl.
*G02B 9/04* (2006.01)
(52) U.S. Cl. ............ 359/793; 359/794; 359/795
(58) Field of Classification Search ........... 359/793, 359/794, 795, 791, 792, 785, 784, 691, 692, 359/770
See application file for complete search history.

(56) References Cited

U.S. PATENT DOCUMENTS
2007/0091456 A1*  4/2007  Yamamoto ............ 359/680

FOREIGN PATENT DOCUMENTS

| JP | 10-260347 | 9/1998 |
|---|---|---|
| JP | 10-260348 | 9/1998 |
| JP | 2000-039553 | 2/2000 |
| JP | 2000-047101 | 2/2000 |
| JP | 2000-089105 | 3/2000 |
| JP | 2003-222793 | 8/2003 |
| JP | 2005-148508 | 6/2005 |
| JP | 2006-521584 | 9/2006 |

OTHER PUBLICATIONS

International Search report dated Jun. 3, 2008 for PCT/JP2008/053239.

* cited by examiner

*Primary Examiner* — Timothy J Thompson
(74) *Attorney, Agent, or Firm* — Pillsbury Winthrop Shaw Pittman, LLP (57) ABSTRACT

An objective optical system includes, in order from the object side, a first unit having two lenses with negative refracting power and positive refracting power, a stop, and a second unit with positive refracting power to satisfy the following condition:

$$3.0 < fb/fL$$

where fb is the back focus of the objective optical system in air and fL is the focal length of the entire objective optical system.

3 Claims, 10 Drawing Sheets

OBJECTIVE OPTICAL SYSTEM FOR ENDOSCOPES

CROSS-REFERENCE TO RELATED APPLICATIONS

This is the U.S. National Stage of PCT/JP2008/053239, filed Feb. 26, 2008, which in turn claims priority to Japanese Patent Application No. 2007-060145, filed Mar. 9, 2007, the entire contents of both applications are incorporated herein by reference in their entireties.

TECHNICAL FIELD

This invention relates to an objective optical system, and in particular, to an objective optical system in which a spectral endoscope provided with a spectral element, such as an etalon, is assumed.

BACKGROUND ART

Conventional objective optical systems for endoscopes are set forth, for example, in Japanese Patent Kokai Nos. Hei 10-260347, Hei 10-260348, 2000-89105, and 2005-148508.

DISCLOSURE OF THE INVENTION

At present, the present applicant is discussing the objective optical system in which the spectral endoscope using the spectral element which is a Fabry-Perot etalon is assumed.

When an endoscope is constructed with the spectral element which is the Fabry-Perot etalon, a desired wavelength of fluorescent light can be observed by a simple operation from an observation part of a different focal length in the body.

However, in the case where the objective optical system applicable to the spectral endoscope is constructed, it is necessary to ensure a long back focus in order to place the Fabry-Perot etalon of the spectral element in the optical path. Moreover, in order to ensure space for placing a driving system driving the etalon and a substrate, it is necessary to increase the overall length of the objective optical system. As a result, a distance from the most object-side lens surface in the objective optical system to the most image-side lens surface becomes long. Further, it is necessary to arrange several filters, such as excitation light cutoff filters, in the optical path of the objective optical system.

However, in each of the conventional objective optical systems for endoscopes exemplified in the above references, sufficient space for placing the etalon in the optical path cannot be ensured. Further, space for placing the filters is narrow and in addition, the driving system cannot be placed.

That is, in the conventional objective optical systems for endoscopes, no objective optical system exists which is applicable to the spectral endoscope.

It is, therefore, an object of the present invention to provide an objective optical system in which space for placing a spectral element, such as an etalon, filters, and a driving system can be sufficiently ensured and the back focus is long and which is applicable to an objective lens for endoscopes of considerable overall length.

In order to achieve the above object, the objective optical system according to the present invention comprises, in order from the object side, a first unit having two lenses with negative refracting power and positive refracting power, a stop, and a second unit with positive refracting power to satisfy the following condition:

$$3.0 < fb/fL \quad (1)$$

where fb is the back focus of the objective optical system in air and fL is the focal length of the entire objective optical system.

The objective optical system according to the present invention comprises, in order from the object side, a first unit having two lenses with negative refracting power and positive refracting power, a stop, and a second unit including a cemented doublet of a positive lens and a negative lens and a positive lens and having a positive refracting power as a whole to satisfy the following condition:

$$1.5 < d12/fL < 4 \quad (2)$$

where d12 is spacing between the most object-side lens and the second most object-side lens in the first unit and fL is the focal length of the entire objective optical system.

In the objective optical system of the present invention, it is desirable to satisfy the following condition:

$$3.0 < fb/fL \quad (1)$$

where fb is the back focus of the objective optical system in air and fL is the focal length of the entire objective optical system.

In the objective optical system of the present invention, it is desirable to satisfy at least one of the following conditions:

$$10 < LTL/fL \quad (3)$$

$$8 < \Sigma d/fL \quad (4)$$

$$0.3 < df/dr < 1.4 \quad (5)$$

$$1.2 < D12/fL < 3 \quad (6)$$

where LTL is the overall length of the objective optical system, fL is the focal length of the entire objective optical system, $\Sigma d$ is a distance from the most object-side lens surface to the most image-side lens surface in the objective optical system, df is spacing between the image-side surface of the most image-side lens in the first unit and the stop, dr is spacing between the stop and the object-side surface of the most object-side lens in the second unit, and D12 is spacing between the first unit and the second unit.

In the objective optical system of the present invention, it is desirable to satisfy the following conditions:

$$-0.12 < fL/f1 < 0.06 \quad (7)$$

$$2.5 < f2/fL < 5.5 \quad (8)$$

where fL is the focal length of the entire objective optical system, f1 is the focal length of the first unit, and f2 is the focal length of the second unit.

In the objective optical system of the present invention, it is desirable that the first unit has a negative refracting power or a weak positive refracting power.

The objective optical system according to the present invention comprises, in order from the object side, a first unit with negative refracting power, a stop, and a second unit with positive refracting power to satisfy the following condition:

$$4.0 < fb/fL \quad (1')$$

where fb is the back focus of the objective optical system in air and fL is the focal length of the entire objective optical system.

In the objective optical system of the present invention, it is desirable to include an objective optical system for endoscopes containing an etalon in the optical path.

According to the present invention, the objective optical system is obtained in which space for placing a spectral element, such as an etalon, filters, and a driving system can be sufficiently ensured and the back focus is long and which is applicable to an objective lens for endoscopes of considerable overall length.

BEST MODE FOR CARRYING OUT THE INVENTION

Before undertaking the description of the embodiments, the function and effect of the present invention will be explained.

The objective optical system of the present invention comprises, in order from the object side, the first unit having two lenses with negative refracting power and positive refracting power, the stop, and the second unit with positive refracting power to satisfy the following condition:

$$3.0 < fb/fL \quad (1)$$

where fb is the back focus of the objective optical system in air and fL is the focal length of the entire objective optical system.

Condition (1) is provided to ensure the back focus.

When Condition (1) is satisfied, the space for placing the etalon and the excitation cutoff filter in the optical path can be ensured. In addition, a distance from the last lens surface to the imaging surface, at which the angle of incidence becomes nearly afocal, can be ensured.

The objective optical system of the present invention comprises, in order from the object side, the first unit having two lenses with negative refracting power and positive refracting power, the stop, and the second unit including the cemented doublet of the positive lens and the negative lens and the positive lens and having the positive refracting power as a whole to satisfy the following condition:

$$1.5 < d12/fL < 4 \quad (2)$$

where d12 is spacing between the most object-side lens and the second most object-side lens in the first unit and fL is the focal length of the entire objective optical system.

Condition (2) is provided to ensure the spacing between the most object-side lens and the second most object-side lens in the first unit. When Condition (2) is satisfied, the space required to arrange an excitation light cutoff filter and a filter for cutting off a particular wavelength, such as a laser wavelength, can be ensured. In addition, between the most object-side lens and the second most object-side lens in the first unit, it becomes easy to make the light afocal.

In the objective optical system of the present invention, it is desirable to satisfy at least one of the following conditions:

$$10 < LTL/fL \quad (3)$$

$$8 < \Sigma d/fL \quad (4)$$

$$0.3 < df/dr < 1.4 \quad (5)$$

$$1.2 < D12/fL < 3 \quad (6)$$

where LTL is the overall length of the objective optical system, fL is the focal length of the entire objective optical system, Σd is a distance from the most object-side lens surface to the most image-side lens surface in the objective optical system, df is spacing between the image-side surface of the most image-side lens in the first unit and the stop, dr is spacing between the stop and the object-side surface of the most object-side lens in the second unit, and d12 is spacing between the first unit and the second unit.

Conditions (3) and (4) refers to the overall length of the objective optical system and the distance from the most object-side lens surface to the most image-side lens surface in the objective optical system.

In order to place the driving system for controlling the etalon in the optical path, it is necessary to ensure the overall length of the objective optical system and a long distance from the most object-side lens surface to the most image-side lens surface in the objective optical system.

When Conditions (3) and (4) are satisfied, the space required to place the driving system for controlling the etalon in the optical path can be ensured.

Condition (5) is provided to maintain lens diameters to proper sizes with respect to spacings between the stop and lenses placed before and behind it. If the upper limit of Condition (5) is exceeded and the spacing between the first unit and the stop is increased, the diameter of the first unit becomes too large. On the other hand, if the lower limit of Condition (5) is passed and the spacing between the stop and the second unit is increased, the diameter of the second unit becomes too large.

Condition (6) is provided to ensure the spacing between the first unit and the second unit. In order to increase the overall length of the objective optical system, it is necessary to increase the spacing between the first unit and the second unit to some extent. When Condition (6) is satisfied, the spacing between the first unit and the second unit can be ensured, there is no need to increase the thickness of each of lenses constituting the objective optical system, and curvature of field can be properly corrected.

In the objective optical system of the present invention, it is desirable to satisfy the following conditions:

$$-0.12 < fL/f1 < 0.06 \quad (7)$$

$$2.5 < f2/fL < 5.5 \quad (8)$$

where fL is the focal length of the entire objective optical system, f1 is the focal length of the first unit, and f2 is the focal length of the second unit.

Condition (7) refers to the refracting power of the first unit. If the refracting power of the first unit becomes high, the ray height of the most object-side lens increases. Consequently, it is desired that the refracting power of the first unit is kept to a minimum. When Condition (7) is satisfied, the refracting power of the first unit can be kept to a minimum.

In the objective optical system of the present invention, it is desirable that the first unit has a negative refracting power or a weak positive refracting power.

The first unit has the negative refracting power or the weak positive refracting power and the second unit has the positive refracting power so as to satisfy condition (7). Whereby, it becomes easy to take the back focus.

Condition (8) refers to the refracting power of the second unit. Beyond the upper limit of Condition (8), the refracting power of the second unit becomes too low and spherical aberration is undercorrected. On the other hand, below the lower limit of Condition (8), the refracting power of the second unit becomes too high, curvature of field deteriorates, and coma is not completely corrected, with the result that bending becomes pronounced.

Embodiment 1

In accordance with the drawings, the embodiments of the objective optical system of the present invention will be explained below.

Figure 1:
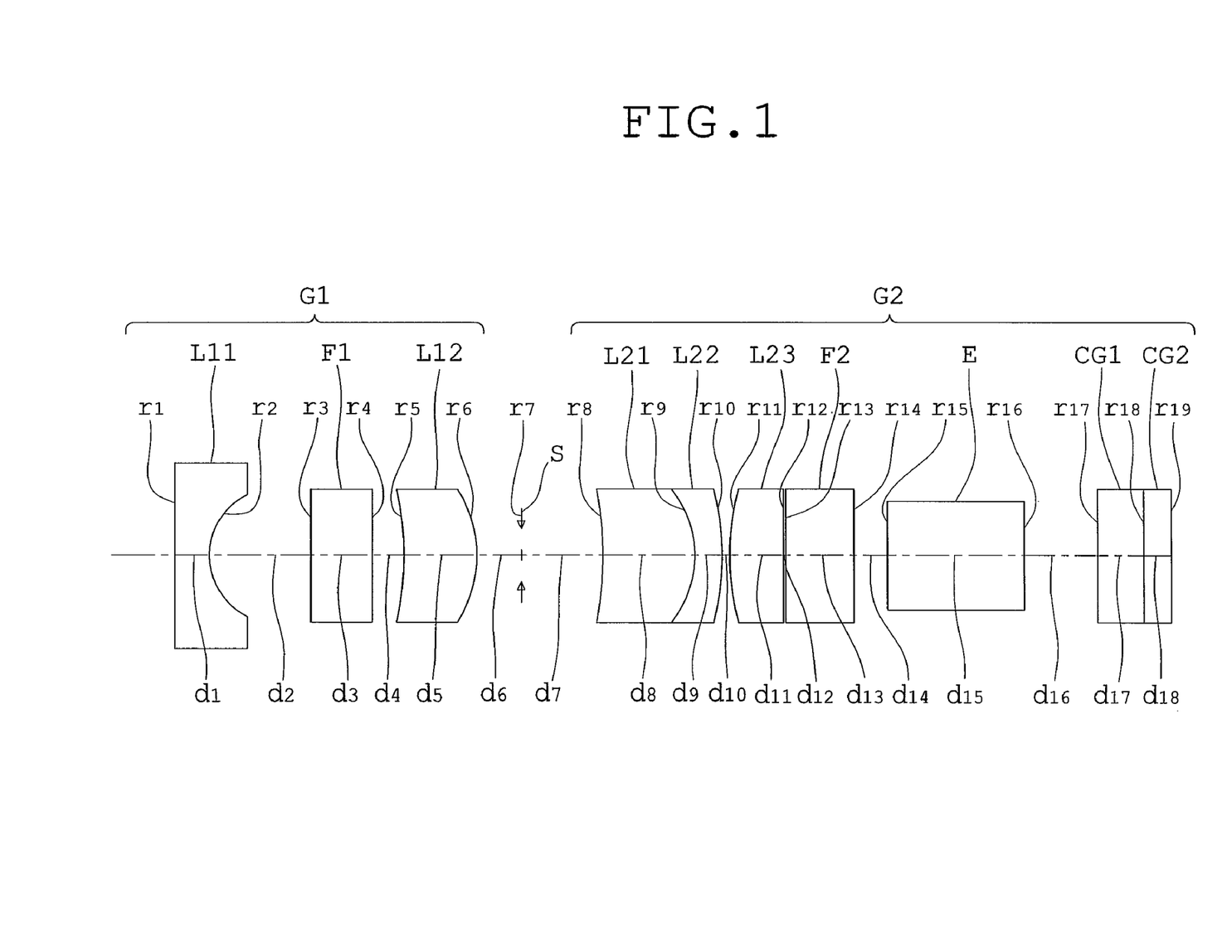
FIG. 1 is a sectional view showing an optical arrangement, developed along the optical axis, of the objective optical system according to Embodiment 1 of the present invention.
Figure 2A:
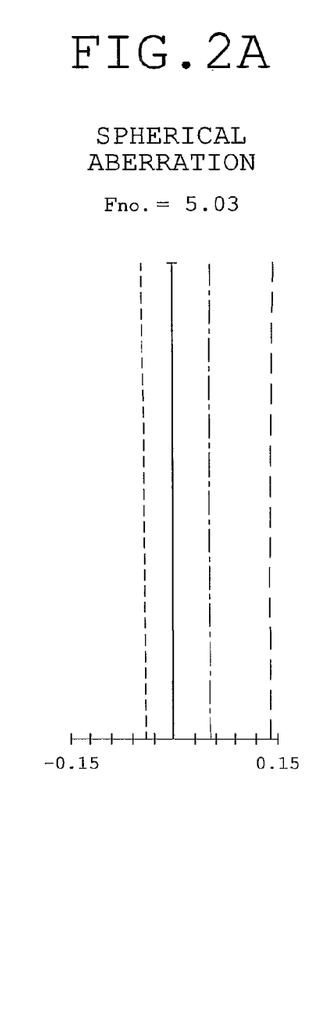
FIGS. 2A, 2B, 2C, and 2D are graphs showing aberration characteristics of the objective optical system in FIG. 1.
Figure 2B:
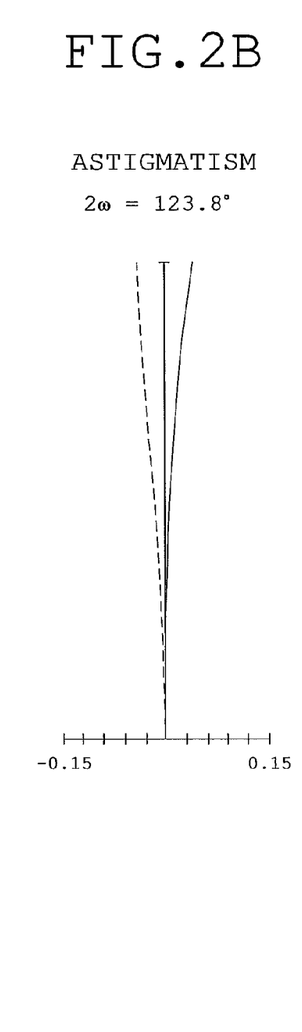
Figure 2C:
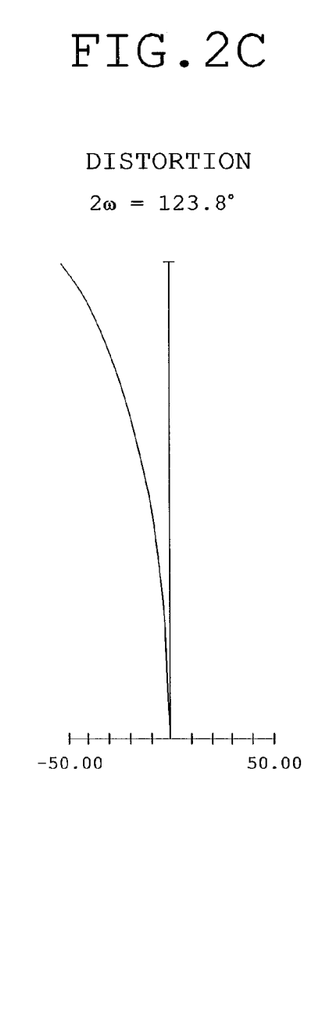
Figure 2D:
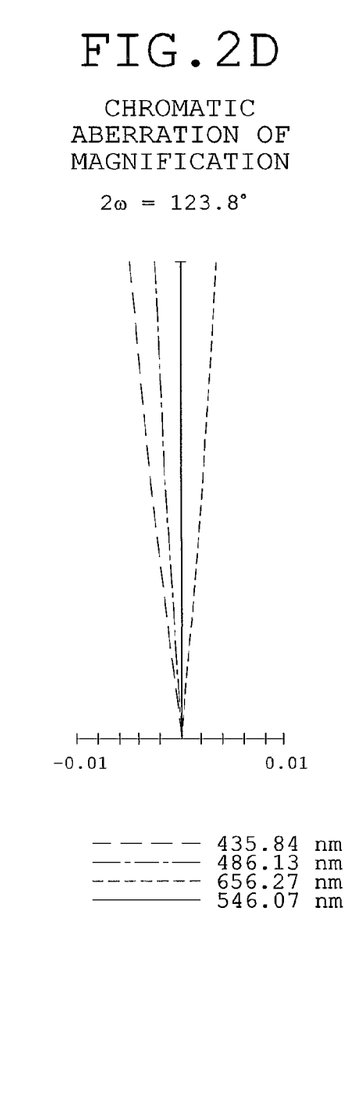

FIG. 1 is a sectional view showing an optical arrangement, developed along the optical axis, of the objective optical system according to Embodiment 1 of the present invention. FIGS. 2A, 2B, 2C, and 2D are graphs showing aberration characteristics of the objective optical system in FIG. 1.

The objective optical system of Embodiment 1 comprises, in order from the object side, a first unit G1, an aperture stop S, and a second unit G2.

The first unit G1 includes a plano-concave lens L11 whose object-side surface is flat and whose image-side surface is concave and a positive meniscus lens L12 with a concave surface facing the object side and has a negative refracting power as a whole. Also, reference symbol F1 represents a filer for cutting off a preset wavelength such as infrared light or excitation light.

The second unit G2 includes a cemented doublet of a positive meniscus lens L21 with a concave surface facing the object side and a negative meniscus lens L22 with a concave surface facing the object side and a plano-convex lens L23 whose object-side surface is convex and whose image-side surface is flat and has a positive refracting power as a whole. Also, reference symbol E represents an etalon and F2 represents a filer for cutting off a preset wavelength such as infrared light or excitation light and symbols CG1 and CG2 represent cover glasses. The etalon E is constructed with two filters conveniently shown as a single optical element.

Subsequently, numerical data of optical members constituting the objective optical system of Embodiment 1 are shown below. Also, in the numerical data, $S_1$, $S_2$, ... denote surface numbers of the optical members constituting the objective optical system; $r_1$, $r_2$, ... denote radii of curvature of the optical members constituting the objective optical system; $d_1$, $d_2$, ... denote face-to-face spacings; $n_{d1}$, $n_{d2}$, ... denote refractive indices of the optical members constituting the objective optical system at the d line; $v_{d1}$, $v_{d2}$, ... denote Abbe's numbers of the optical members constituting the objective optical system at the d line; FNO denotes an F-number; and 2ω denotes the total angle of view. Also, these symbols are also used for the numerical data of other embodiments to be described later.

Numerical data 1 (Embodiment 1)
Object point distance: 15.00 mm
Focal length: 1.00 mm
FNO: 5.03
2ω: 123.8°

| | | | | |
|---|---|---|---|---|
| $S_1$ | $r_1 = \infty$ | $d_1 = 0.534$ | $n_{d1} = 1.883$ | $v_{d1} = 40.78$ |
| $S_2$ | $r_2 = 1.0771$ | $d_2 = 1.603$ | | |
| $S_3$ | $r_3 = \infty$ | $d_3 = 0.96$ | $n_{d3} = 1.52287$ | $v_{d3} = 59.89$ |
| $S_4$ | $r_4 = \infty$ | $d_4 = 0.5$ | | |
| $S_5$ | $r_5 = -5.0365$ | $d_5 = 1.153$ | $n_{d5} = 1.51742$ | $v_{d5} = 52.43$ |
| $S_6$ | $r_6 = -1.9783$ | $d_6 = 0.7$ | | |
| $S_7$ (Stop) | $r_7 = \infty$ | $d_7 = 1.274$ | | |
| $S_8$ | $r_8 = -6.4027$ | $d_8 = 1.473$ | $n_{d8} = 1.7725$ | $v_{d8} = 49.6$ |
| $S_9$ | $r_9 = -1.6377$ | $d_9 = 0.427$ | $n_{d9} = 1.92286$ | $v_{d9} = 18.9$ |
| $S_{10}$ | $r_{10} = -4.4491$ | $d_{10} = 0.128$ | | |
| $S_{11}$ | $r_{11} = 4.1866$ | $d_{11} = 0.854$ | $n_{d11} = 1.834$ | $v_{d11} = 37.16$ |
| $S_{12}$ | $r_{12} = \infty$ | $d_{12} = 0.033$ | | |
| $S_{13}$ | $r_{13} = \infty$ | $d_{13} = 1.068$ | $n_{d13} = 1.52287$ | $v_{d13} = 59.89$ |
| $S_{14}$ | $r_{14} = \infty$ | $d_{14} = 0.534$ | | |
| $S_{15}$ | $r_{15} = \infty$ | $d_{15} = 2.135$ | $n_{d15} = 1.54886$ | $v_{d15} = 67.84$ |
| $S_{16}$ | $r_{16} = \infty$ | $d_{16} = 1.163$ | | |
| $S_{17}$ | $r_{17} = \infty$ | $d_{17} = 0.747$ | $n_{d17} = 1.51633$ | $v_{d17} = 64.14$ |
| $S_{18}$ | $r_{18} = \infty$ | $d_{18} = 0.427$ | $n_{d18} = 1.52287$ | $v_{d18} = 59.89$ |
| $S_{19}$ | $r_{19} = \infty$ | | | |

Embodiment 2

Figure 3:
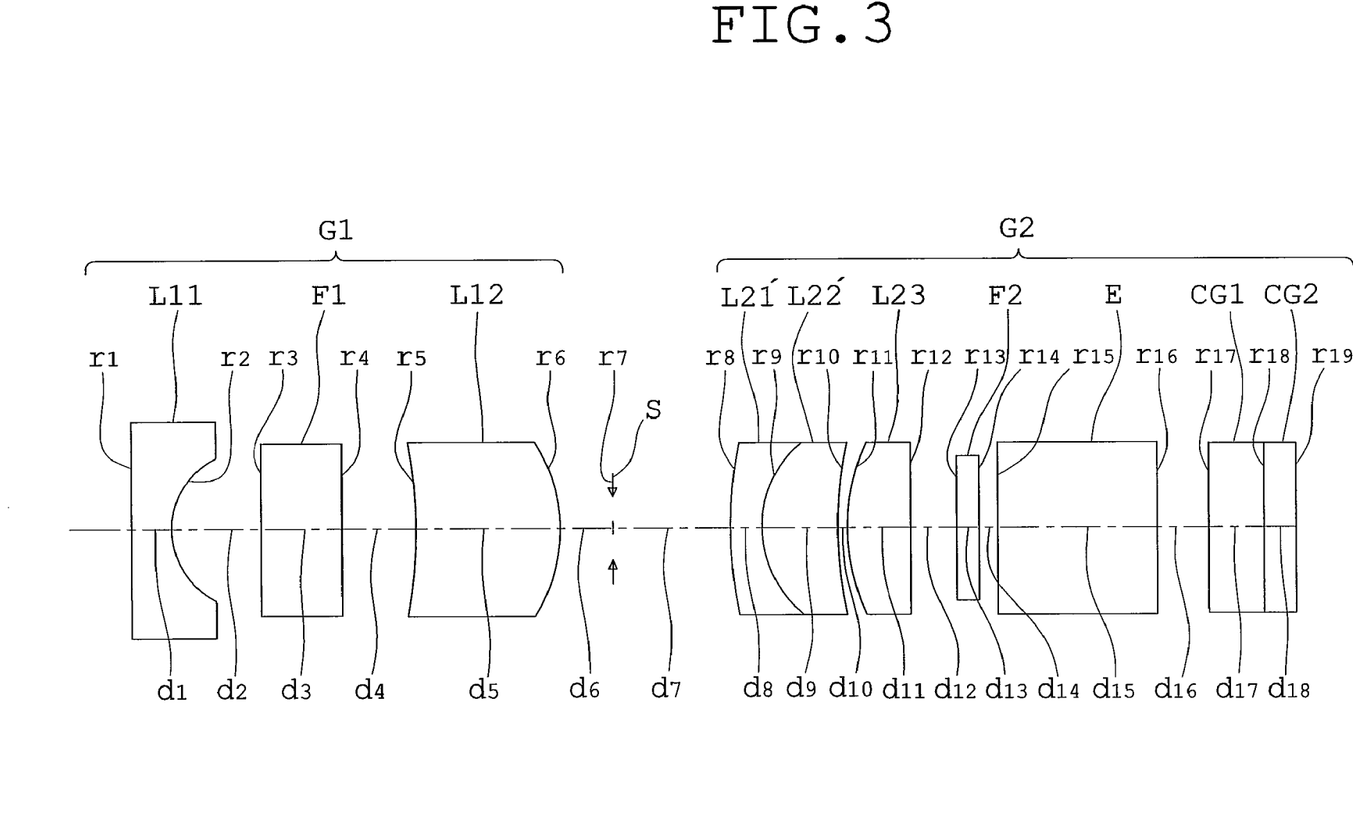
FIG. 3 is a sectional view showing an optical arrangement, developed along the optical axis, of the objective optical system according to Embodiment 2 of the present invention.
Figure 4A:
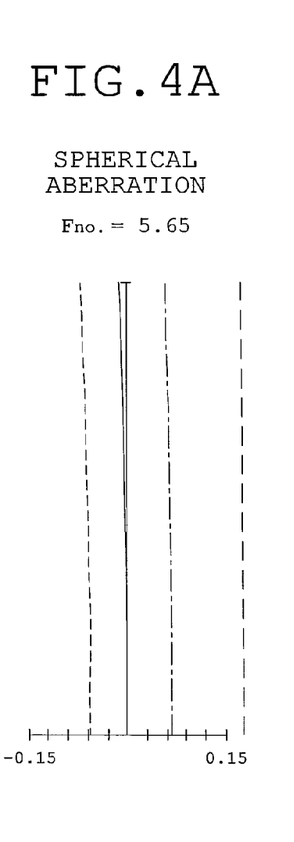
FIGS. 4A, 4B, 4C, and 4D are graphs showing aberration characteristics of the objective optical system in FIG. 3.
Figure 4B:
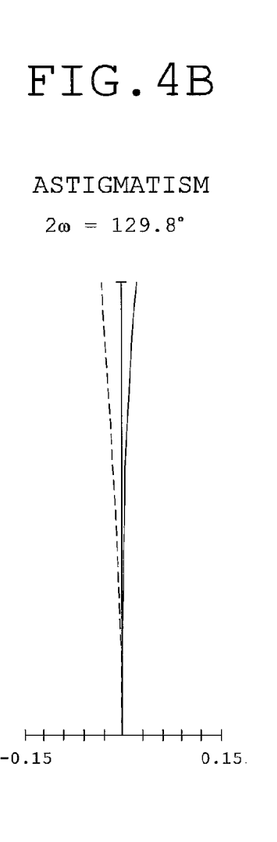
Figure 4C:
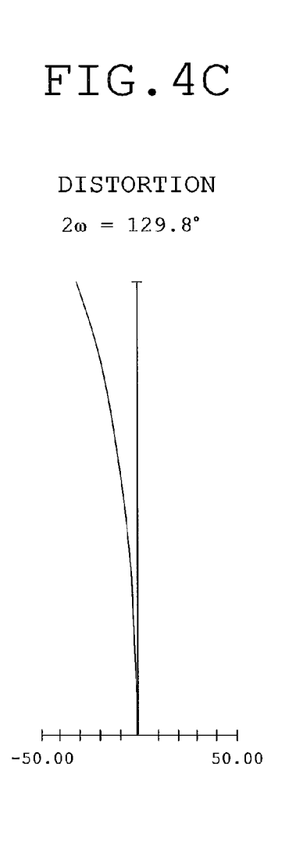
Figure 4D:
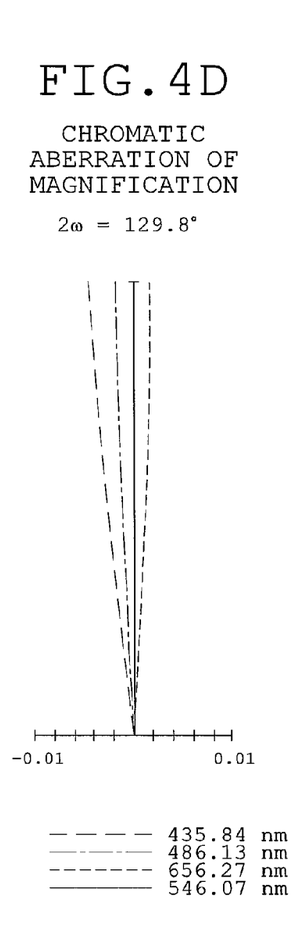

FIG. 3 is a sectional view showing an optical arrangement, developed along the optical axis, of the objective optical system according to Embodiment 2 of the present invention. FIGS. 4A, 4B, 4C, and 4D are graphs showing aberration characteristics of the objective optical system in FIG. 3.

The objective optical system of Embodiment 2 comprises, in order from the object side, the first unit G1, the aperture stop S, and the second unit G2.

The first unit G1 includes the plano-concave lens L11 whose object-side surface is flat and whose image-side surface is concave and the positive meniscus lens L12 with a concave surface facing the object side and has a negative refracting power as a whole.

Also, reference symbol F1 represents a filer for cutting off a preset wavelength such as infrared light or excitation light.

The second unit G2 includes a cemented doublet of a negative meniscus lens L21' with a convex surface facing the object side and a positive meniscus lens L22' with a convex surface facing the object side and the plano-convex lens L23 whose object-side surface is convex and whose image-side surface is flat and has a positive refracting power as a whole. Also, reference symbol E represents an etalon and F2 represents a filer for cutting off a preset wavelength such as infrared light or excitation light and symbols CG1 and CG2 represent cover glasses. The etalon E is constructed with two filters conveniently shown as a single optical element.

Subsequently, numerical data of optical members constituting the objective optical system of Embodiment 2 are shown below.

Numerical data 2 (Embodiment 2)
Object point distance: 15.20 mm
Focal length: 1.00 mm
FNO: 5.65
2ω: 129.8°

| | | | | |
|---|---|---|---|---|
| $S_1$ | $r_1 = \infty$ | $d_1 = 0.542$ | $n_{d1} = 1.88814$ | $v_{d1} = 40.78$ |
| $S_2$ | $r_2 = 1.1226$ | $d_2 = 1.219$ | | |
| $S_3$ | $r_3 = \infty$ | $d_3 = 1.084$ | $n_{d3} = 1.52498$ | $v_{d3} = 59.89$ |
| $S_4$ | $r_4 = \infty$ | $d_4 = 1.023$ | | |

-continued

Numerical data 2 (Embodiment 2)
Object point distance: 15.20 mm
Focal length: 1.00 mm
FNO: 5.65
2ω: 129.8°

| | | | | |
|---|---|---|---|---|
| $S_5$ | $r_5 = -5.845$ | $d_5 = 1.95$ | $n_{d5} = 1.51977$ | $v_{d5} = 52.43$ |
| $S_6$ | $r_6 = -2.3042$ | $d_6 = 0.715$ | | |
| $S_7$ (Stop) | $r_7 = \infty$ | $d_7 = 1.61$ | | |
| $S_8$ | $r_8 = 5.1091$ | $d_8 = 0.433$ | $n_{d8} = 1.93429$ | $v_{d8} = 18.9$ |
| $S_9$ | $r_9 = 1.5361$ | $d_9 = 1.04$ | $n_{d9} = 1.77621$ | $v_{d9} = 49.6$ |
| $S_{10}$ | $r_{10} = 5.1885$ | $d_{10} = 0.13$ | | |
| $S_{11}$ | $r_{11} = 2.9042$ | $d_{11} = 0.867$ | $n_{d11} = 1.83932$ | $v_{d11} = 37.16$ |
| $S_{12}$ | $r_{12} = \infty$ | $d_{12} = 0.636$ | | |
| $S_{13}$ | $r_{13} = \infty$ | $d_{13} = 0.299$ | $n_{d13} = 1.52498$ | $v_{d13} = 59.89$ |
| $S_{14}$ | $r_{14} = \infty$ | $d_{14} = 0.266$ | | |
| $S_{15}$ | $r_{15} = \infty$ | $d_{15} = 2.167$ | $n_{d15} = 1.55079$ | $v_{d15} = 67.84$ |
| $S_{16}$ | $r_{16} = \infty$ | $d_{16} = 0.71$ | | |
| $S_{17}$ | $r_{17} = \infty$ | $d_{17} = 0.758$ | $n_{d17} = 1.51825$ | $v_{d17} = 64.14$ |
| $S_{18}$ | $r_{18} = \infty$ | $d_{18} = 0.434$ | $n_{d18} = 1.52498$ | $v_{d18} = 59.89$ |
| $S_{19}$ | $r_{19} = \infty$ | | | |

Embodiment 3

Figure 5:
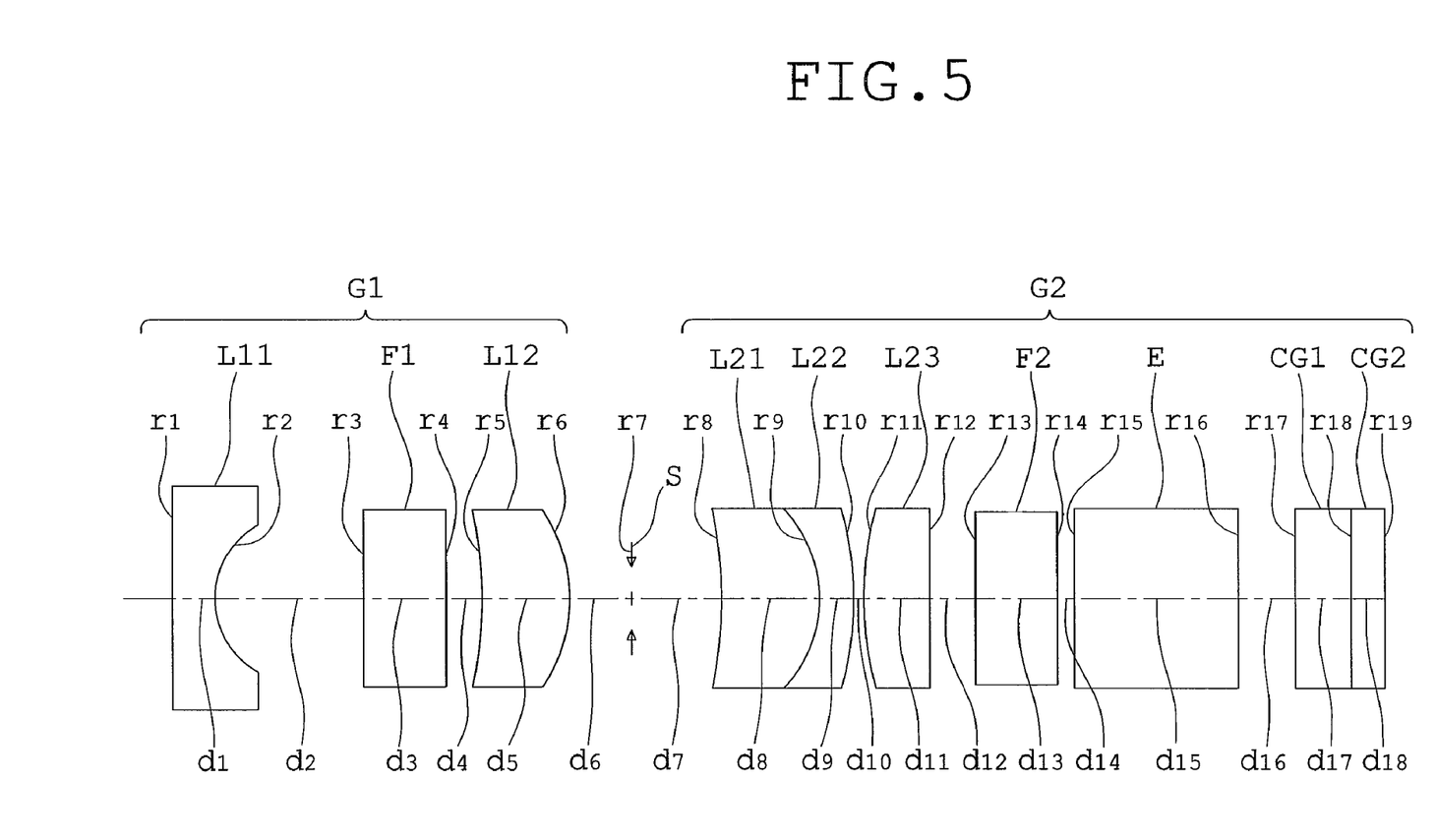
FIG. 5 is a sectional view showing an optical arrangement, developed along the optical axis, of the objective optical system according to Embodiment 3 of the present invention.
Figure 6A:
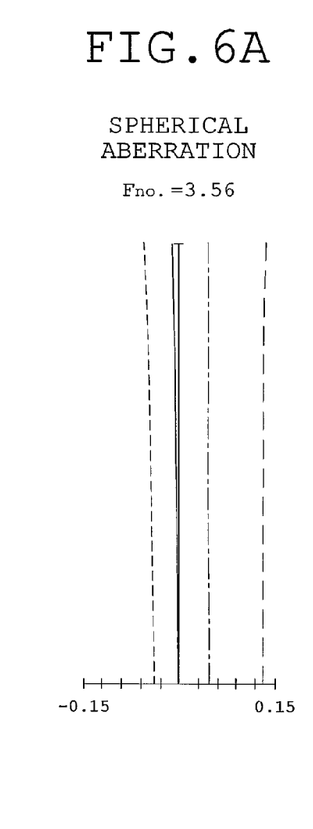
FIGS. 6A, 6B, 6C, and 6D are graphs showing aberration characteristics of the objective optical system in FIG. 5.
Figure 6B:
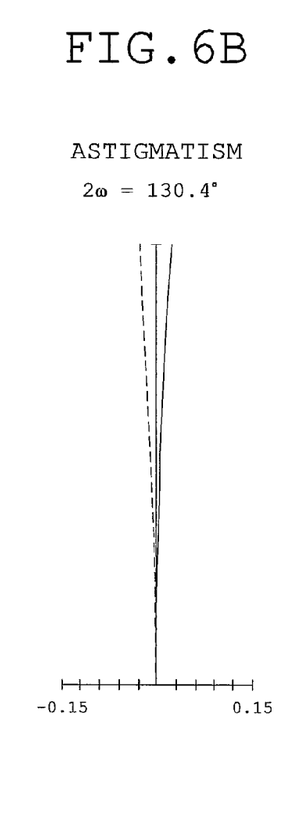
Figure 6C:
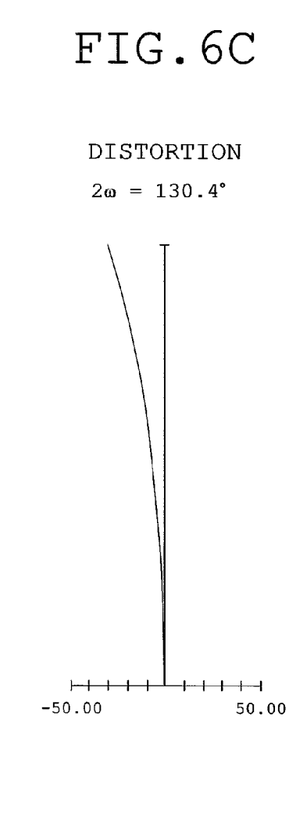
Figure 6D:
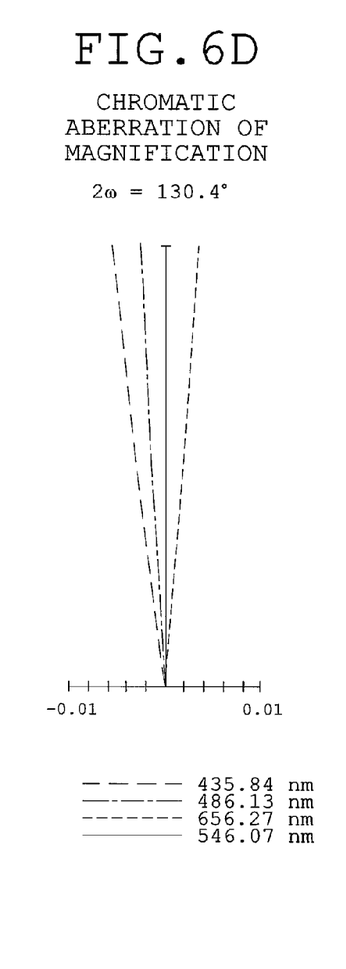

FIG. 5 is a sectional view showing an optical arrangement, developed along the optical axis, of the objective optical system according to Embodiment 3 of the present invention. FIGS. 6A, 6B, 6C, and 6D are graphs showing aberration characteristics of the objective optical system in FIG. 5.

The objective optical system of Embodiment 3 comprises, in order from the object side, the first unit G1, the aperture stop S, and the second unit G2.

The first unit G1 includes the plano-concave lens L11 whose object-side surface is flat and whose image-side surface is concave and the positive meniscus lens L12 with a concave surface facing the object side and has a negative refracting power as a whole. Also, reference symbol F1 represents a filer for cutting off a preset wavelength such as infrared light or excitation light.

The second unit G2 includes the cemented doublet of the positive meniscus lens L21 with a concave surface facing the object side and the negative meniscus lens L22 with a concave surface facing the object side and the plano-convex lens L23 whose object-side surface is convex and whose image-side surface is flat and has a positive refracting power as a whole. Also, reference symbol E represents an etalon and F2 represents a filer for cutting off a preset wavelength such as infrared light or excitation light and symbols CG1 and CG2 represent cover glasses. The etalon E is constructed with two filters conveniently shown as a single optical element.

Subsequently, numerical data of optical members constituting the objective optical system of Embodiment 3 are shown below.

Numerical data 3 (Embodiment 3)
Object point distance: 15.3 mm
Focal length: 1.001 mm
FNO: 3.56
2ω: 130.4°

| | | | | |
|---|---|---|---|---|
| $S_1$ | $r_1 = \infty$ | $d_1 = 0.547$ | $n_{d1} = 1.883$ | $v_{d1} = 40.78$ |
| $S_2$ | $r_2 = 1.1488$ | $d_2 = 1.967$ | | |
| $S_3$ | $r_3 = \infty$ | $d_3 = 1.094$ | $n_{d3} = 1.52287$ | $v_{d3} = 59.89$ |
| $S_4$ | $r_4 = \infty$ | $d_4 = 0.458$ | | |
| $S_5$ | $r_5 = -6.0644$ | $d_5 = 1.175$ | $n_{d5} = 1.51742$ | $v_{d5} = 52.43$ |
| $S_6$ | $r_6 = -2.128$ | $d_6 = 0.805$ | | |
| $S_7$ (Stop) | $r_7 = \infty$ | $d_7 = 1.204$ | | |
| $S_8$ | $r_8 = -6.6898$ | $d_8 = 1.313$ | $n_{d8} = 1.7725$ | $v_{d8} = 49.6$ |

-continued

Numerical data 3 (Embodiment 3)
Object point distance: 15.3 mm
Focal length: 1.001 mm
FNO: 3.56
2ω: 130.4°

| | | | | |
|---|---|---|---|---|
| $S_9$ | $r_9 = -1.6377$ | $d_9 = 0.438$ | $n_{d9} = 1.92286$ | $v_{d9} = 18.9$ |
| $S_{10}$ | $r_{10} = -4.686$ | $d_{10} = 0.131$ | | |
| $S_{11}$ | $r_{11} = 4.1786$ | $d_{11} = 0.875$ | $n_{d11} = 1.834$ | $v_{d11} = 37.16$ |
| $S_{12}$ | $r_{12} = \infty$ | $d_{12} = 0.609$ | | |
| $S_{13}$ | $r_{13} = \infty$ | $d_{13} = 1.1$ | $n_{d13} = 1.52287$ | $v_{d13} = 59.89$ |
| $S_{14}$ | $r_{14} = \infty$ | $d_{14} = 0.225$ | | |
| $S_{15}$ | $r_{15} = \infty$ | $d_{15} = 2.18$ | $n_{d15} = 1.54886$ | $v_{d15} = 67.84$ |
| $S_{16}$ | $r_{16} = \infty$ | $d_{16} = 0.741$ | | |
| $S_{17}$ | $r_{17} = \infty$ | $d_{17} = 0.75$ | $n_{d17} = 1.51633$ | $v_{d17} = 64.14$ |
| $S_{18}$ | $r_{18} = \infty$ | $d_{18} = 0.438$ | $n_{d18} = 1.52287$ | $v_{d18} = 59.89$ |
| $S_{19}$ | $r_{19} = \infty$ | | | |

Embodiment 4

Figure 7:
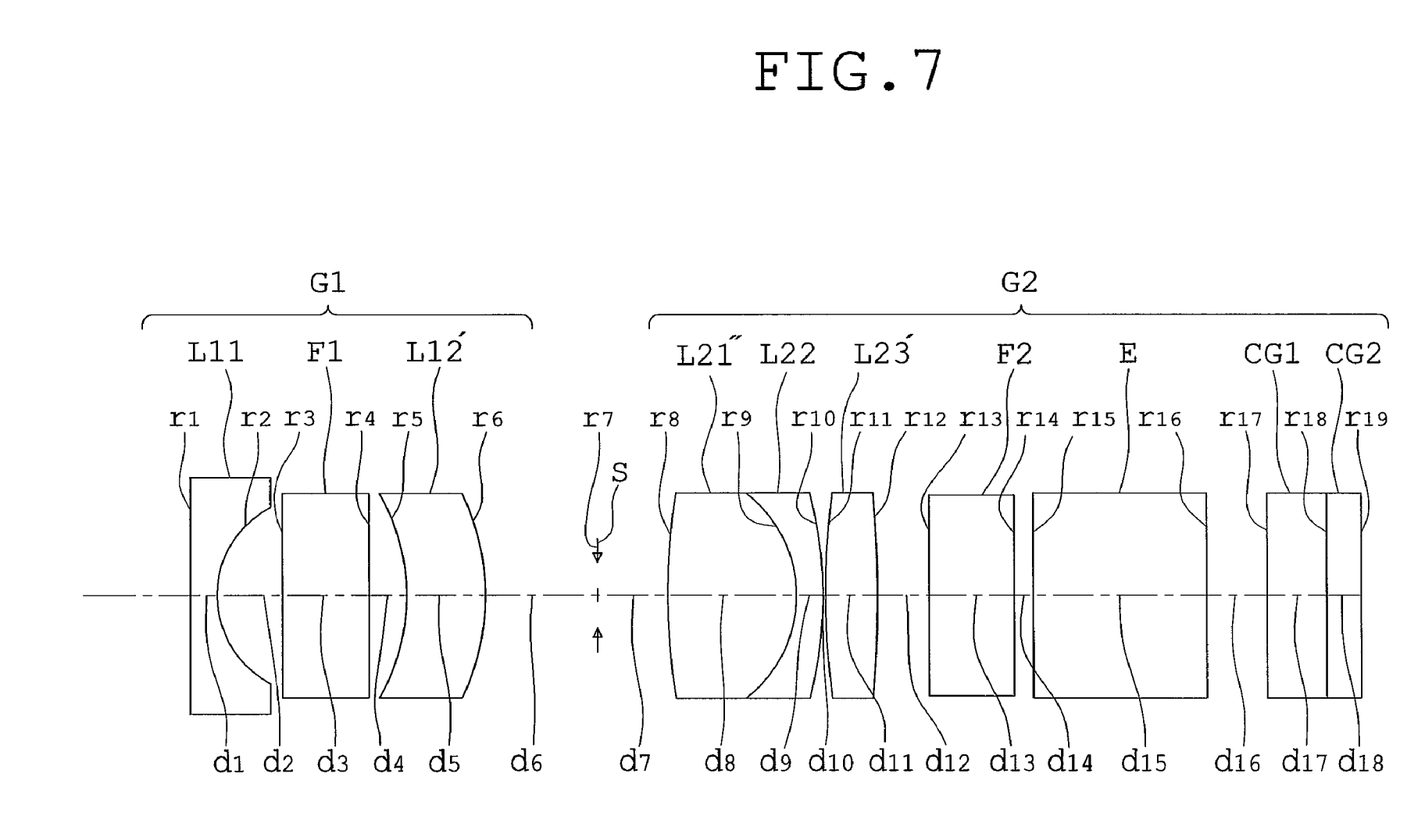
FIG. 7 is a sectional view showing an optical arrangement, developed along the optical axis, of the objective optical system according to Embodiment 4 of the present invention.
Figure 8A:
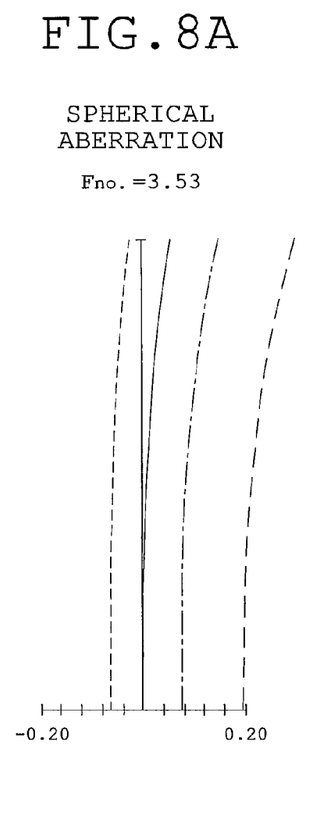
FIGS. 8A, 8B, 8C, and 8D are graphs showing aberration characteristics of the objective optical system in FIG. 7.
Figure 8B:
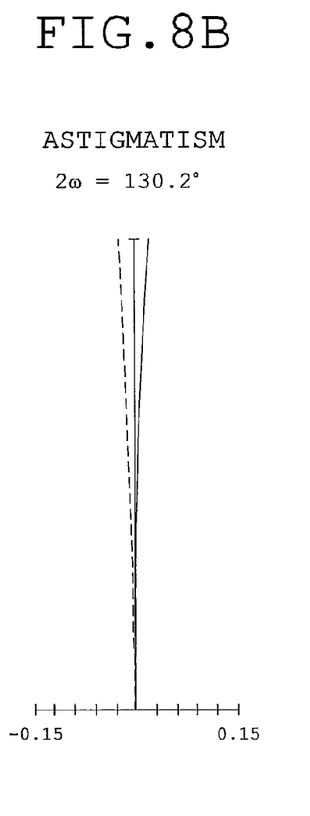
Figure 8C:
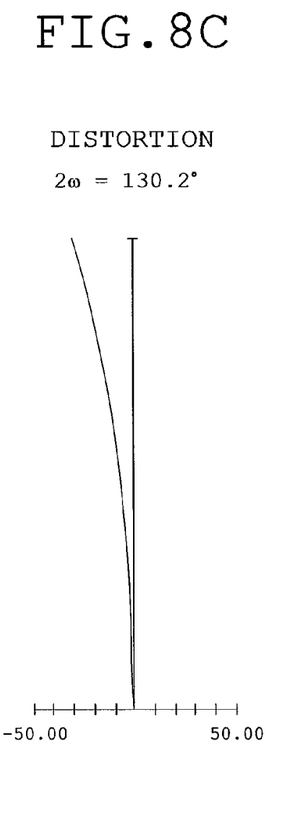
Figure 8D:
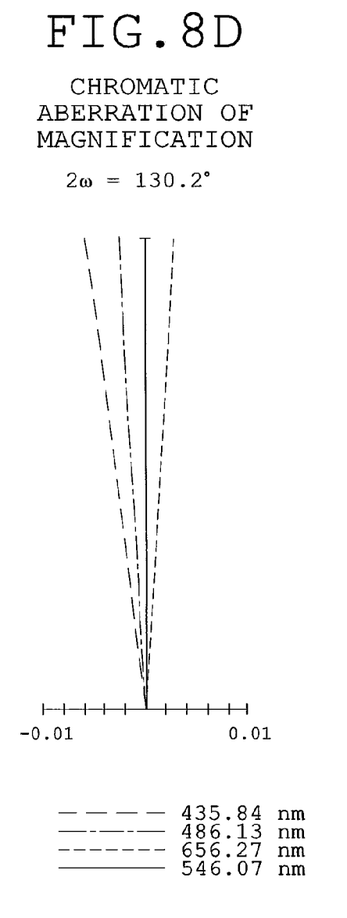

FIG. 7 is a sectional view showing an optical arrangement, developed along the optical axis, of the objective optical system according to Embodiment 4 of the present invention. FIGS. 8A, 8B, 8C, and 8D are graphs showing aberration characteristics of the objective optical system in FIG. 7.

The objective optical system of Embodiment 4 comprises, in order from the object side, the first unit G1, the aperture stop S, and the second unit G2.

The first unit G1 includes the plano-concave lens L11 whose object-side surface is flat and whose image-side surface is concave and a negative meniscus lens L12' with a concave surface facing the object side and has a negative refracting power as a whole.

Also, reference symbol F1 represents a filer for cutting off a preset wavelength such as infrared light or excitation light.

The second unit G2 includes a cemented doublet of a biconvex L21" and the negative meniscus lens L22 with a concave surface facing the object side and a bi-convex lens L23' and has a positive refracting power as a whole. Also, reference symbol E represents an etalon and F2 represents a filer for cutting off a preset wavelength such as infrared light or excitation light and symbols CG1 and CG2 represent cover glasses. The etalon E is constructed with two filters conveniently shown as a single optical element.

Subsequently, numerical data of optical members constituting the objective optical system of Embodiment 4 are shown below.

Numerical data 4 (Embodiment 4)
Object point distance: 15.80 mm
Focal length: 1.00 mm
FNO: 3.53
2ω: 130.2°

| | | | | |
|---|---|---|---|---|
| $S_1$ | $r_1 = \infty$ | $d_1 = 0.339$ | $n_{d1} = 1.883$ | $v_{d1} = 40.78$ |
| $S_2$ | $r_2 = 1.322$ | $d_2 = 0.864$ | | |
| $S_3$ | $r_3 = \infty$ | $d_3 = 1.128$ | $n_{d3} = 1.52287$ | $v_{d3} = 59.89$ |
| $S_4$ | $r_4 = \infty$ | $d_4 = 0.484$ | | |
| $S_5$ | $r_5 = -2.6542$ | $d_5 = 1.01$ | $n_{d5} = 1.51742$ | $v_{d5} = 52.43$ |
| $S_6$ | $r_6 = -3.3443$ | $d_6 = 1.369$ | | |
| $S_7$ (Stop) | $r_7 = \infty$ | $d_7 = 1.023$ | | |
| $S_8$ | $r_8 = 7.6736$ | $d_8 = 1.702$ | $n_{d8} = 1.7725$ | $v_{d8} = 49.6$ |
| $S_9$ | $r_9 = -1.702$ | $d_9 = 0.339$ | $n_{d9} = 1.92286$ | $v_{d9} = 18.9$ |
| $S_{10}$ | $r_{10} = -5.564$ | $d_{10} = 0.023$ | | |
| $S_{11}$ | $r_{11} = 7.5107$ | $d_{11} = 0.692$ | $n_{d11} = 1.834$ | $v_{d11} = 37.16$ |
| $S_{12}$ | $r_{12} = -17.1324$ | $d_{12} = 0.677$ | | |
| $S_{13}$ | $r_{13} = \infty$ | $d_{13} = 1.128$ | $n_{d13} = 1.52287$ | $v_{d13} = 59.89$ |
| $S_{14}$ | $r_{14} = \infty$ | $d_{14} = 0.253$ | | |

-continued

Numerical data 4 (Embodiment 4)
Object point distance: 15.80 mm
Focal length: 1.00 mm
FNO: 3.53
2ω: 130.2°

| | | | | |
|---|---|---|---|---|
| $S_{15}$ | $r_{15} = \infty$ | $d_{15} = 2.258$ | $n_{d15} = 1.54886$ | $v_{d15} = 67.84$ |
| $S_{16}$ | $r_{16} = \infty$ | $d_{16} = 0.79$ | | |
| $S_{17}$ | $r_{17} = \infty$ | $d_{17} = 0.79$ | $n_{d17} = 1.51633$ | $v_{d17} = 64.14$ |
| $S_{18}$ | $r_{18} = \infty$ | $d_{18} = 0.452$ | $n_{d18} = 1.52287$ | $v_{d18} = 59.89$ |
| $S_{19}$ | $r_{19} = \infty$ | | | |

Embodiment 5

Figure 9:
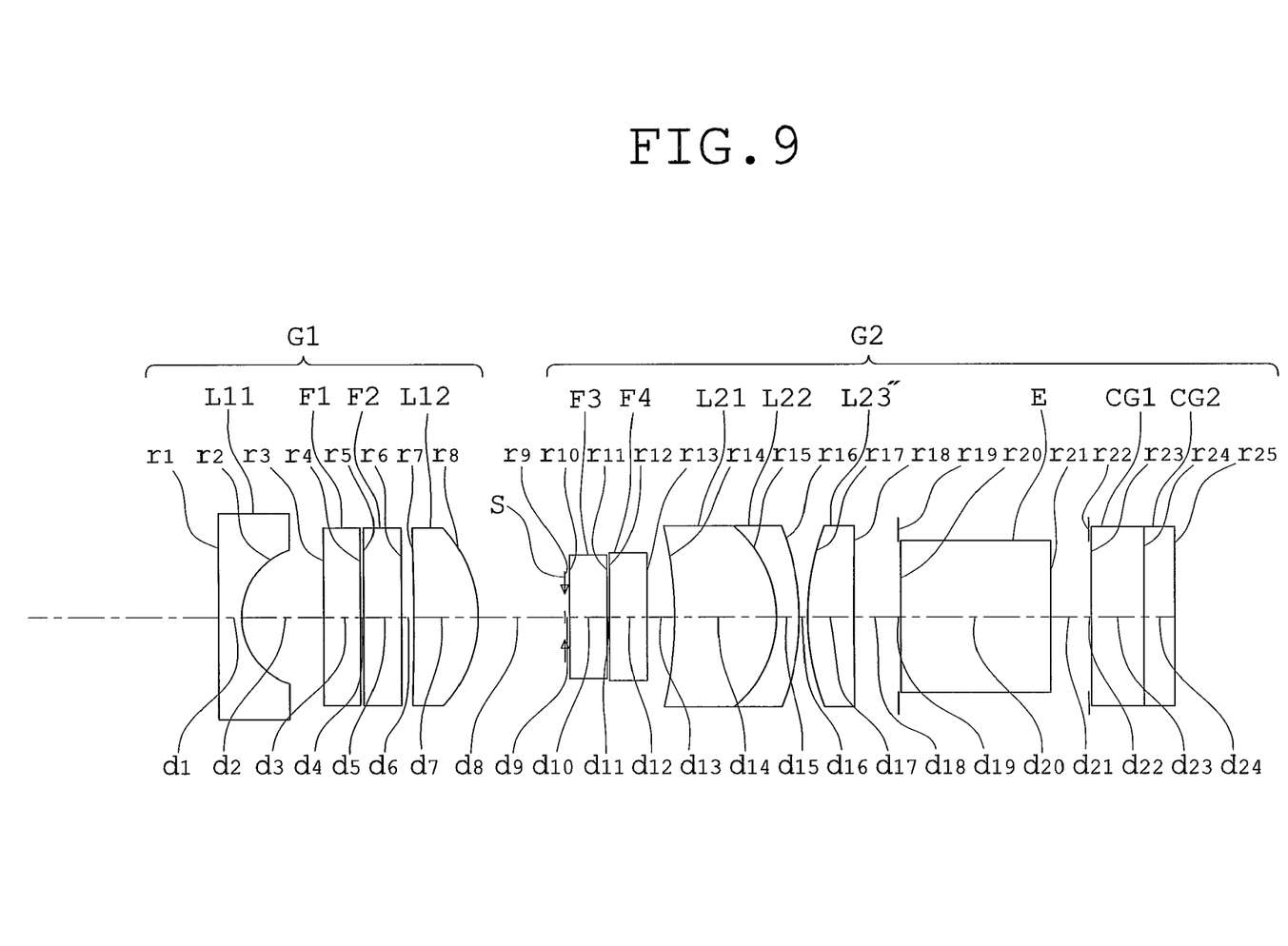
FIG. 9 is a sectional view showing an optical arrangement, developed along theoptical axis, of the objective optical system according to Embodiment 5 of the present invention.
Figure 10A:
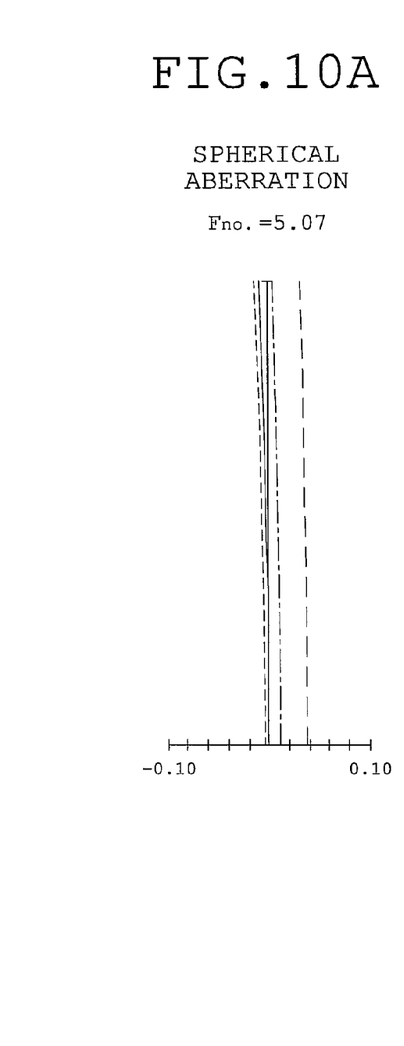
FIGS. 10A, 10B, 10C, and 10D are graphs showing aberration characteristics of the objective optical system in FIG. 9.
Figure 10B:
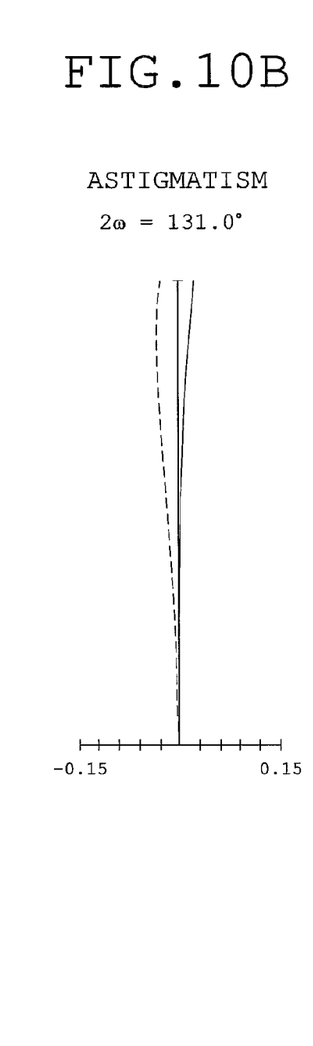
Figure 10C:
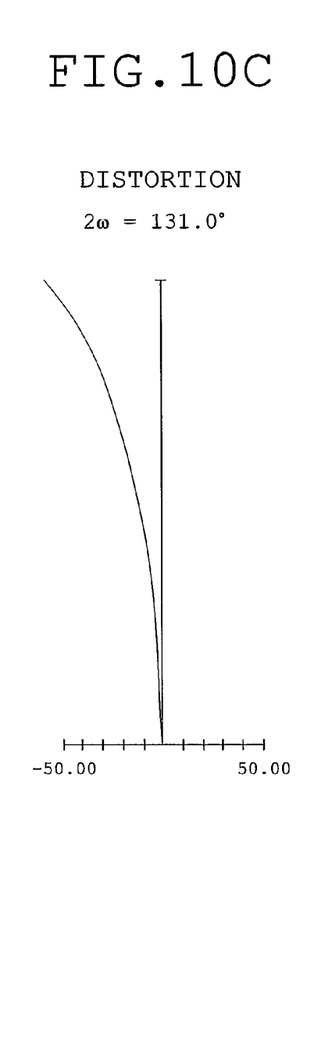
Figure 10D:
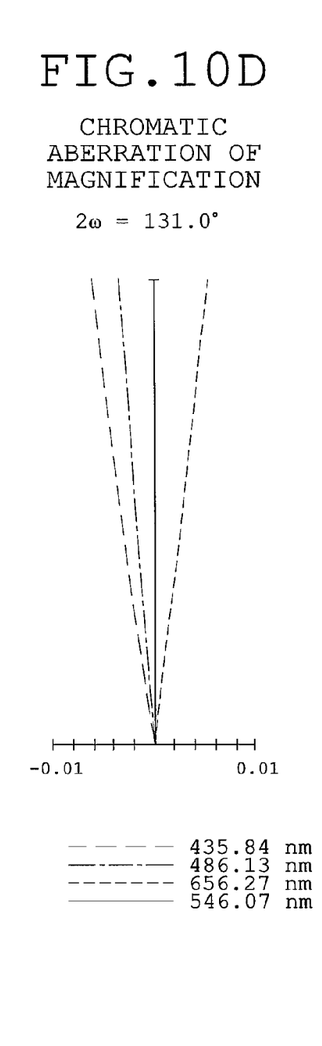

FIG. 9 is a sectional view showing an optical arrangement, developed along the optical axis, of the objective optical system according to Embodiment 5 of the present invention. FIGS. 10A, 10B, 10C, and 10D are graphs showing aberration characteristics of the objective optical system in FIG. 9.

The objective optical system of Embodiment 5 comprises, in order from the object side, the first unit G1, the aperture stop S, and the second unit G2.

The first unit G1 includes the plano-concave lens L11 whose object-side surface is flat and whose image-side surface is concave and the positive meniscus lens L12 with a concave surface facing the object side and has a weak positive refracting power as a whole. Also, reference symbols F1 and F2 represent filers for cutting off preset wavelengths such as infrared light or excitation light.

The second unit G2 includes the cemented doublet of the positive meniscus lens L21 with a concave surface facing the object side and the negative meniscus lens L22 with a concave surface facing the object side and a positive meniscus lens L23" with a convex surface facing the object side and has a positive refracting power as a whole. Also, reference symbol E represents an etalon and symbols F3 and F4 represent filers for cutting off preset wavelengths such as infrared light or excitation light and CG1 and CG2 represent cover glasses. The etalon E is constructed with two filters conveniently shown as a single optical element.

Subsequently, numerical data of optical members constituting the objective optical system of Embodiment 5 are shown below.

Numerical data 5 (Embodiment 5)
Object point distance: 15.40 mm
Focal length: 1.00 mm
FNO: 5.07
2ω: 131.0°

| | | | | |
|---|---|---|---|---|
| $S_1$ | $r_1 = \infty$ | $d_1 = 0.33$ | $n_{d1} = 1.88814$ | $v_{d1} = 40.78$ |
| $S_2$ | $r_2 = 1.0491$ | $d_2 = 1.188$ | | |
| $S_3$ | $r_3 = \infty$ | $d_3 = 0.55$ | $n_{d3} = 1.52498$ | $v_{d3} = 59.89$ |
| $S_4$ | $r_4 = \infty$ | $d_4 = 0.033$ | | |
| $S_5$ | $r_5 = \infty$ | $d_5 = 0.55$ | $n_{d5} = 1.52498$ | $v_{d5} = 59.89$ |
| $S_6$ | $r_6 = \infty$ | $d_6 = 0.186$ | | |
| $S_7$ | $r_7 = -32.7113$ | $d_7 = 0.93$ | $n_{d7} = 1.51977$ | $v_{d7} = 52.43$ |
| $S_8$ | $r_8 = -1.9245$ | $d_8 = 1.28$ | | |
| $S_9$ (Stop) | $r_9 = 0.055$ | | | |
| $S_{10}$ | $r_{10} = \infty$ | $d_{10} = 0.55$ | $n_{d10} = 1.52498$ | $v_{d10} = 59.89$ |
| $S_{11}$ | $r_{11} = \infty$ | $d_{11} = 0.033$ | | |
| $S_{12}$ | $r_{12} = \infty$ | $d_{12} = 0.55$ | $n_{d12} = 1.52498$ | $v_{d12} = 59.89$ |
| $S_{13}$ | $r_{13} = \infty$ | $d_{13} = 0.411$ | | |
| $S_{14}$ | $r_{14} = -5.4467$ | $d_{14} = 1.494$ | $n_{d14} = 1.77621$ | $v_{d14} = 49.6$ |
| $S_{15}$ | $r_{15} = -1.6589$ | $d_{15} = 0.33$ | $n_{d15} = 1.93429$ | $v_{d15} = 18.9$ |
| $S_{16}$ | $r_{16} = -3.6629$ | $d_{16} = 0.11$ | | |
| $S_{17}$ | $r_{17} = 3.5282$ | $d_{17} = 0.687$ | $n_{d17} = 1.83932$ | $v_{d17} = 37.16$ |
| $S_{18}$ | $r_{18} = 37.6018$ | $d_{18} = 0.65$ | | |

-continued

Numerical data 5 (Embodiment 5)
Object point distance: 15.40 mm
Focal length: 1.00 mm
FNO: 5.07
2ω: 131.0°

| | | | | |
|---|---|---|---|---|
| $S_{19}$ | $r_{19} = \infty$ | $d_{19} = 0.033$ | | |
| $S_{20}$ | $r_{20} = \infty$ | $d_{20} = 2.2$ | $n_{d20} = 1.55079$ | $v_{d20} = 67.84$ |
| $S_{21}$ | $r_{21} = \infty$ | $d_{21} = 0.55$ | | |
| $S_{22}$ | $r_{22} = \infty$ | $d_{22} = 0.033$ | | |
| $S_{23}$ | $r_{23} = \infty$ | $d_{23} = 0.77$ | $n_{d23} = 1.51825$ | $v_{d23} = 64.14$ |
| $S_{24}$ | $r_{24} = \infty$ | $d_{24} = 0.44$ | $n_{d24} = 1.52498$ | $v_{d24} = 59.89$ |
| $S_{25}$ | $r_{25} = \infty$ | | | |

Subsequently, values corresponding to parameters in the conditions of the above individual embodiments are shown in Table 1.

TABLE 1

| Condition parameter | Embodiment 1 | Embodiment 2 | Embodiment 3 | Embodiment 4 | Embodiment 5 |
|---|---|---|---|---|---|
| (1) fb/fL | 4.52 | 3.907 | 4.422 | 4.677 | 3.41 |
| (2) d12/fL | 2.732 | 2.956 | 3.14 | 2.088 | 2.123 |
| (3) df/dr | 0.549 | 0.444 | 0.669 | 1.338 | 1.049 |
| (4) fL/f1 | −0.076 | −0.023 | −0.03 | −0.647 | 0.011 |
| (5) f2/fL | 4.075 | 4.673 | 4.215 | 3.244 | 3.329 |
| (6) LTL/fL | 15.708 | 15.869 | 16.034 | 15.319 | 13.902 |
| (7) D12/fL | 1.973 | 2.327 | 2.007 | 2.392 | 2.5 |
| (8) Σd/fL | 9.603 | 10.622 | 9.997 | 8.972 | 9.242 |

INDUSTRIAL APPLICABILITY

The objective optical system of the present invention is useful in the field in which it is desired that the objective optical system for endoscopes using the spectral element, such as an etalon, notably in the field of medicine of a surgical microscope.

The invention claimed is:

1. An objective optical system comprising, in order from an object side:
   a first unit having two lenses with negative refracting power and positive refracting power;
   a stop; and
   a second unit with positive refracting power,
   wherein the objective optical system satisfies the following condition:

$$3.0 < fb/fL$$

where fb is a back focus of the objective optical system in air and fL is a focal length of the entire objective optical system, and
   wherein the objective optical system further satisfies at least one of the following conditions:

$$10 < LTL/fL$$

$$8 < \Sigma d/fL$$

$$0.3 < df/dr < 1.4$$

$$1.2 < D12/fL < 3$$

where LTL is an overall length of the objective optical system, Σd is a distance from a most object-side lens surface to a most image-side lens surface in the objective optical system, df is spacing between an image-side surface of a most image-side lens in the first unit and the stop, dr is spacing between the stop and an object-side surface of a most object-side lens in the second unit, and D12 is spacing between the first unit and the second unit.

2. An objective optical system comprising, in order from an object side:
   a first unit having two lenses with negative refracting power and positive refracting power;
   a stop; and
   a second unit with positive refracting power,
   wherein the objective optical system satisfies the following condition:

$$3.0 < fb/fL$$

where fb is a back focus of the objective optical system in air and fL is a focal length of an entire objective optical system, and
   wherein the objective optical system further satisfies the following conditions:

$$-0.12 < fL/f1 < 0.06$$

$$2.5 < f2/fL < 5.5$$

where f1 is a focal length of the first unit, and f2 is a focal length of the second unit.

3. An objective optical system comprising, in order from an object side:
   a first unit having two lenses with negative refracting power and positive refracting power;
   a stop; and
   a second unit with positive refracting power,
   wherein the objective optical system satisfies the following condition:

$$3.0 < fb/fL$$

where fb is a back focus of the objective optical system in air and fL is a focal length of an entire objective optical system, and
   wherein the objective optical system is configured as an objective optical system for endoscopes that includes an etalon in an optical path.

* * * * *